United States Patent
Ichikawa et al.

(10) Patent No.: US 7,682,072 B2
(45) Date of Patent: Mar. 23, 2010

(54) METHOD OF MEASURING THERMAL CONDUCTIVITY OF HONEYCOMB STRUCTURE

(75) Inventors: Shuichi Ichikawa, Handa (JP); Aiko Otsuka, Okazaki (JP); Motomichi Itou, Handa (JP); Takuma Makino, Kasugai (JP)

(73) Assignee: NGK Insulators, Ltd., Nagoya (JP)

( * ) Notice: Subject to any disclaimer, the term of this patent is extended or adjusted under 35 U.S.C. 154(b) by 741 days.

(21) Appl. No.: 10/505,334

(22) PCT Filed: Mar. 14, 2003

(86) PCT No.: PCT/JP03/03083

§ 371 (c)(1),
(2), (4) Date: Aug. 23, 2004

(87) PCT Pub. No.: WO03/078988

PCT Pub. Date: Sep. 25, 2003

(65) Prior Publication Data
US 2005/0105584 A1 May 19, 2005

(30) Foreign Application Priority Data
Mar. 20, 2002 (JP) .............................. 2002-077557

(51) Int. Cl.
*G01N 25/18* (2006.01)
(52) U.S. Cl. ......................................... 374/44; 374/141
(58) Field of Classification Search ................... 374/29, 374/30, 43–45, 10, 4, 5, 50, 111, 112, 135, 374/137, 57; 73/25.01, 25.03
See application file for complete search history.

(56) References Cited

U.S. PATENT DOCUMENTS

| | | | | |
|---|---|---|---|---|
| 3,238,775 A | * | 3/1966 | Watts | 374/30 |
| 4,155,244 A | * | 5/1979 | Bhattacharyya | 374/44 |
| 4,553,852 A | * | 11/1985 | Derderian et al. | 374/1 |
| 4,577,976 A | * | 3/1986 | Hayashi et al. | 374/29 |
| 4,630,938 A | * | 12/1986 | Piorkowska-Palczewska et al. | 374/44 |
| 4,850,713 A | * | 7/1989 | Thery et al. | 374/30 |
| 5,270,092 A | * | 12/1993 | Griffith et al. | 428/69 |
| 5,297,868 A | * | 3/1994 | Graebner | 374/44 |
| 5,693,685 A | * | 12/1997 | Kishimoto et al. | 521/130 |
| 5,846,276 A | * | 12/1998 | Nagai et al. | 55/523 |
| 5,940,784 A | * | 8/1999 | El-Husayni | 702/130 |
| 6,142,662 A | * | 11/2000 | Narh et al. | 374/44 |
| 6,183,128 B1 | * | 2/2001 | Beran et al. | 374/44 |
| 6,331,075 B1 | * | 12/2001 | Amer et al. | 374/44 |

(Continued)

FOREIGN PATENT DOCUMENTS

EP     1 184 066 A1     3/2002

(Continued)

*Primary Examiner*—Gail Verbitsky
(74) *Attorney, Agent, or Firm*—Oliff & Berridge, PLC

(57) ABSTRACT

The method for measurement of thermal conductivity of a honeycomb structure according to the present invention comprises the steps keeping the whole honeycomb structure in a steady temperature state with keeping two ends of the honeycomb structure at given different temperatures; and measuring a thermal conductivity of the honeycomb structure in the steady state. According to the present invention there is provided a method for measurement of thermal conductivity of a honeycomb structure, which can measure the thermal conductivity of a honeycomb structure in the shape of the honeycomb structure per se or in a predetermined block shape without preparing, for example, a test specimen of particular shape.

8 Claims, 1 Drawing Sheet

U.S. PATENT DOCUMENTS

| | | | |
|---|---|---|---|
| 6,408,256 B1 * | 6/2002 | Hittle et al. | 702/130 |
| 6,730,421 B1 * | 5/2004 | Kirino et al. | 428/831.2 |
| 6,896,405 B2 * | 5/2005 | Osone et al. | 374/43 |
| 6,984,253 B2 * | 1/2006 | Ichikawa et al. | 55/484 |
| 7,104,681 B2 * | 9/2006 | Naranjo Carvajal | 374/143 |
| 2001/0036531 A1 | 11/2001 | Shinohara et al. | |
| 2002/0136261 A1 * | 9/2002 | Naka et al. | 374/44 |
| 2003/0196788 A1 * | 10/2003 | Vinegar et al. | 166/57 |
| 2004/0101030 A1 * | 5/2004 | Trapasso et al. | 374/165 |
| 2005/0020704 A1 * | 1/2005 | Iwasa et al. | 521/86 |
| 2005/0126140 A1 * | 6/2005 | Ito et al. | 55/523 |
| 2005/0199367 A1 * | 9/2005 | Romahn | 165/80.3 |
| 2006/0051556 A1 * | 3/2006 | Ohno et al. | 428/116 |
| 2006/0059877 A1 * | 3/2006 | Yoshida | 55/523 |

FOREIGN PATENT DOCUMENTS

| | | |
|---|---|---|
| JP | 54123082 A * | 9/1979 |
| JP | A-07-060116 | 3/1995 |
| JP | A-09-070513 | 3/1997 |
| JP | A 2000-329718 | 11/2000 |
| JP | A 2001-21512 | 1/2001 |

* cited by examiner

METHOD OF MEASURING THERMAL CONDUCTIVITY OF HONEYCOMB STRUCTURE

TECHNICAL FIELD

The present invention relates to a method for measurement of thermal conductivity of a honeycomb structure, which can measure the thermal conductivity of a honeycomb structure in the shape of the honeycomb structure per se without preparing a test specimen or the like.

BACKGROUND ART

Honeycomb structures (honeycomb filters) made of a ceramic are in use in order to capture the dust or another particulate matter contained in, for example, the exhaust gas emitted from automobiles (particularly, diesel engine automobiles) or the incineration gas generating during the incineration of waste, or to recover a product or a raw material from the high-temperature waste gas emitted in production processes of various industries. These honeycomb structures have a large number of through-holes surrounded by partition walls and extending in the axial direction of a honeycomb structure; the partition walls surrounding the through-holes have a filtration ability; a given number of the through-holes are plugged at one end of a honeycomb structure and the remaining through-holes are plugged at the other end of a honeycomb structure; thus, the honeycomb structures are formed so as to enable the capture and removal of the particulate matter contained in a dust-containing fluid. The ceramic-made honeycomb structures are superior in heat resistance and corrosion resistance and have suitable properties as a filter material used in a high temperature, corrosive gas atmosphere and, therefore, are in use for purification of various exhaust or waste gases.

A high-temperature exhaust or waste gas is often passed through such a honeycomb structure and, in that case, the honeycomb structure generates a thermal strain in various forms depending upon its thermal conductivity. Hence, in designing a honeycomb structure, it is necessary to grasp its thermal conductivity. However, since the honeycomb structure has a special construction, there has heretofore been established no method for measuring the thermal conductivity of the honeycomb structure per se without preparing a test specimen or the like.

As the method for measuring the thermal conductivity of a fine ceramic, there is, for example, a laser flash method which is specified in JIS R 1611. This method has restrictions; for example, the method is restricted to a material having a porosity of 10% or less and also to a test specimen of flat plate having, for example, a square shape of 10 mm×10 mm or less. Therefore, this method has been unable to apply to any honeycomb structure because of its material and shape. Further, the method has had an operational problem because a test specimen need be prepared.

The present invention has been made in view of the above-mentioned problems and aims at providing a method for measurement of thermal conductivity of a honeycomb structure which can measure the thermal conductivity of a honeycomb structure in the shape of the honeycomb structure per se or in a predetermined block shape without preparing, for example, a test specimen of particular shape.

DISCLOSURE OF THE INVENTION

In order to achieve the above aim, the present invention provides the following method for measurement of thermal conductivity of a honeycomb structure.

[1] A method for measurement of thermal conductivity of a honeycomb structure, the method comprising the steps of:
keeping the whole honeycomb structure in a steady temperature state with keeping two ends of the honeycomb structure at given different temperatures; and
measuring a thermal conductivity of the honeycomb structure in the steady state.

[2] The method for measurement of thermal conductivity of a honeycomb structure set forth in the above [1], wherein contact members kept at given different temperatures are contacted with the two ends of the honeycomb structure to keep the two ends of the honeycomb structure at given different temperatures.

[3] The method for measurement of thermal conductivity of a honeycomb structure set forth in the above [2], wherein the thermal conductivity $\lambda$ (W/mK) of the honeycomb structure is calculated from the following expression (1):

$$\lambda = QH \cdot [L/(T1-T2)] \qquad (1)$$

where the thermal conductivity $\lambda$(W/mK) of the honeycomb structure is specified in relation to:
an amount of heat flow QH (W/m$^2$)=[(Q1+Q2)/2], each of Q1 (W/m$^2$) and Q2 (W/m$^2$) being obtained by measuring an amount of heat flow at each contact member using a heat flow meter connected with the contact member;
a distance L (m) between the two ends of the honeycomb structure; and
temperatures T1 (K) and T2 (K) of the two ends of the honeycomb structure in the steady temperature state of the whole honeycomb structure.

[4] The method for measurement of thermal conductivity of a honeycomb structure set forth in the above [2] or [3], wherein the two ends of the honeycomb structure and the contact members are contacted with each other via high-thermal-conductivity members.

[5] The method for measurement of thermal conductivity of a honeycomb structure set forth in the above [4], wherein a sheet having flexibility is used as the high-thermal-conductivity member.

[6] The method for measurement of thermal conductivity of a honeycomb structure set forth in the above [4] or [5], wherein the high-thermal-conductivity member is made of a film formed by applying a paste containing a substance of high thermal conductivity, on a contact face of the honeycomb structure and/or the contact member.

[7] The method for measurement of thermal conductivity of a honeycomb structure set forth in any of the above [2] to [6], wherein a contact pressure between the contact member and the end of the honeycomb structure is set at 1 to 10 kg/cm$^2$.

[8] The method for measurement of thermal conductivity of a honeycomb structure set forth in any of the above [1] to [7], wherein an exposed portion of the side of the honeycomb structure is covered with a heat-insulating material.

[9] The method for measurement of thermal conductivity of a honeycomb structure set forth in any of the above [1] to [8], wherein the honeycomb structure is made of a material having a thermal conductivity of 1 (W/mK) or more.

[10] The method for measurement of thermal conductivity of a honeycomb structure set forth in any of the above [1] to [9], wherein the honeycomb structure contains at least one kind selected from the group consisting of silicon carbide, a composite of silicon carbide and metallic silicon, and silicon nitride.

BEST MODE FOR CARRYING OUT THE INVENTION

In the method for measurement of thermal conductivity of a honeycomb structure according to the present invention, the thermal conductivity of a honeycomb structure is measured with keeping the whole honeycomb structure in a steady temperature state; thereby, the thermal conductivity can be measured easily with, for example, a cylindrical honeycomb structure per se or a block of predetermined size cut out therefrom, irrespective of the shape of the honeycomb structure to be measured and it is not necessary to prepare a test specimen of particular shape.

The embodiments of the present invention are described specifically below with reference to the accompanying drawings. However, the present invention is not restricted to the following embodiments and it should be construed that appropriate design changes, improvements, etc. can be added based on the ordinary knowledge of those skilled in the art, unless they deviate from the gist of the present invention.

Figure 1:
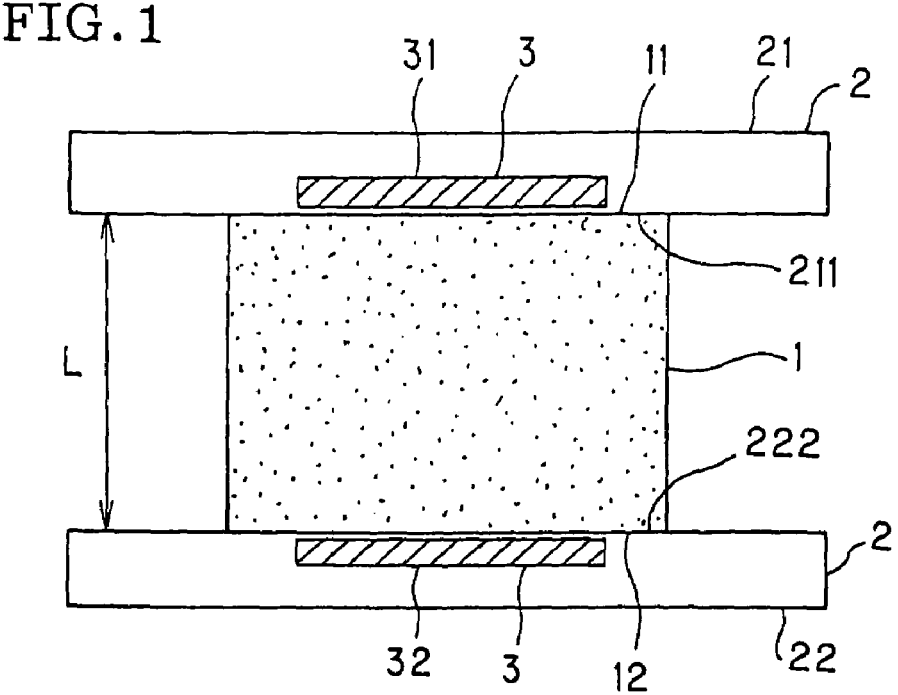
FIG. 1 is a side view showing a honeycomb structure and contact members which are in contact with the two ends of the honeycomb structure, in one embodiment of the method for measurement of thermal conductivity of a honeycomb structure according to the present invention.

FIG. 1 is a side view showing a honeycomb structure and contact members which are in contact with the two ends of the honeycomb structure, in one embodiment of the method for measurement of thermal conductivity of a honeycomb structure according to the present invention.

In the present embodiment, in order to measure the thermal conductivity of a honeycomb structure, at first, the two ends of the honeycomb structure in its axial direction are kept at given different temperatures. To achieve it, contact members 2 (21 and 22) kept at respective given temperatures are contacted with the two ends 11 and 12 of a honeycomb structure 1 in its axial direction, as shown in FIG. 1. By thus contacting the contact members 21 and 22 kept at respective given temperatures, with the two ends 11 and 12 of the honeycomb structure 1 in its axial direction, the two ends 11 and 12 can be kept at given different temperatures and thereby the whole honeycomb structure 1 can be kept in a steady temperature state.

Next, there is determined an amount of heat flow QH in the honeycomb structure 1 being kept in a steady temperature state. The amount of heat flow QH is determined by measuring the amounts of heat flows Q1 and Q2 respectively flowing through the contact members 21 and 22 by the use of heat flow meters 3 (31 and 32) connected beforehand to the contact members 21 and 22 which are in contact with the two ends 11 and 12 of the honeycomb structure 1 in a steady temperature state and then making calculation using an expression of QH=(Q1+Q2)/2.

In the present embodiment, the thermal conductivity A (W/mK) of the honeycomb structure 1 is calculated from the following expression (1) wherein the thermal conductivity A (W/mK) of the honeycomb structure is specified in relation to:

the above-obtained amount of heat flow QH (W/m$^2$)[= (Q1+Q2)/2] in the honeycomb structure 1 in a steady temperature state, a distance L (m) between the two ends of the honeycomb structure 1, and temperatures T1 (k) and T2 (K) of the two ends 11 and 12 of the honeycomb structure 1 in the steady temperature state of the whole honeycomb structure.

$$\lambda = QH \cdot [L/(T1-T2)] \quad (1)$$

Thus, measurement of thermal conductivity is made with the whole honeycomb structure being kept in a steady temperature state; therefore, the measurement of thermal conductivity can be made easily with, for example, a cylindrical honeycomb structure per se or a block of predetermined size cut out therefrom, irrespective of the shape of the honeycomb structure to be measured and it is not necessary to prepare a test specimen of particular shape.

Such a method for measurement of thermal conductivity is called a steady method (JIS A 1412) but has not been applied to honeycomb structures.

In the present embodiment, it is preferred that the thermal contact between each end (11, 12) of the honeycomb structure 1 and each contact member (21, 22) is made as good as possible and the thermal conduction between the contact member 21 and the end 11 of the honeycomb structure 1 as well as between the end 12 of the honeycomb structure 1 and the contact member 22 is made as high as possible without heat loss. The losses of the amount of heat flow in these areas are regarded as indicating a barrier of the thermal conduction of the honeycomb structure per se and, therefore, may decrease the accuracy of measurement of the thermal conductivity of the honeycomb structure. For example, when, in the contact between the face of the end 11 of the honeycomb structure and the contact face 211 of the contact member 21, many (wide) gaps are formed owing to, for example, the fine surface unevennesses of the face and the contact face, thermal conduction may be difficult. Further, when the honeycomb structure is made of a material of high thermal conductivity, the decrease in the accuracy of measurement may be large.

For higher accuracy of measurement of thermal conductivity, it is preferred that the heat dissipation from the exposed portion of the side of the honeycomb structure 1 when a heat flows through the honeycomb structure 1, is as small as possible.

Figure 2:
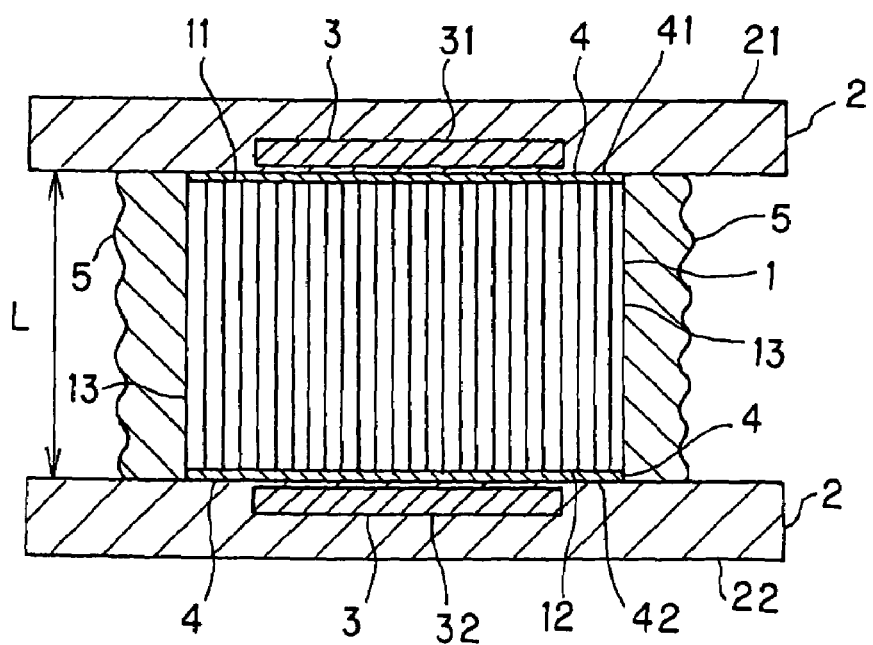
FIG. 2 is a sectional view of a honeycomb structure, contact members, etc. along a plane including the axis of the honeycomb structure, in another embodiment of the method for measurement of thermal conductivity of a honeycomb structure according to the present invention.

FIG. 2 is a sectional view of a honeycomb structure, contact members, etc. along a plane including the axis of the honeycomb structure, in another embodiment for carrying out the method for measurement of thermal conductivity of a honeycomb structure according to the present invention.

In order, as mentioned above, for the thermal contact between each end (11, 12) of the honeycomb structure 1 and each contact member (21, 22) to be made as good as possible and for the thermal conduction between the contact member 21 and the end 11 of the honeycomb structure 1 as well as between the end 12 of the honeycomb structure 1 and the contact member 22 to be made as high as possible with minimum heat loss, it was conducted, as shown in FIG. 2, to contact the contact member 21 with the end 11 of the honeycomb structure via a high-thermal-conductivity member 41 and contact the contact member 22 with the end 12 of the honeycomb structure via a high-thermal-conductivity member 42. By thus contacting each contact member (21, 22) with each end (11, 12) of the honeycomb structure via each high-thermal-conductivity member (41, 42), the gap formed in the contact between the face of the end 11 of the honeycomb structure and the contact face 211 of the contact member 21 owing to, for example, the fine surface unevennesses of the face and the contact face, becomes less because of the use of the high-thermal-conductivity member 4. Thereby, thermal conduction is improved and the measurement of thermal conductivity of a honeycomb structure can be made at higher accuracy. Since the high-thermal-conductivity member 4 has a high thermal conductivity, measurement of thermal conductivity of a honeycomb structure with the member 4 being present between each end (11, 12) of a honeycomb structure and each contact member (21, 22) gives no large measurement error.

The high-thermal-conductivity member 4 is preferred to be a flexible sheet. This flexible sheet can be deformed into the shape of the above-mentioned gap formed between the two contact faces and can fill the gap, whereby good thermal conduction is obtained. As the material for the high-thermal-conductivity member 4 of a flexible sheet, there is preferred a carbon sheet or a metal foil of aluminum, copper or the like. The high-thermal conductivity member 4 is preferred to be as thin as possible relative to the test specimen used, in order to minimize the influence on measured thermal conductivity value. When the influence of the thickness of the high-thermal-conductivity member 4 on the measured thermal conductivity value λ is not negligible owing to the thickness relation of the high-thermal-conductivity member 4 and the test specimen (honeycomb structure 1), a corrected thermal conductivity $\lambda 1$ (W/mK) of the test specimen (honeycomb structure 1) is calculated according to the following expression (2) using the thermal conductivity $\lambda 2$ (W/mK) and thickness L2 (m) of the material for the high-thermal-conductivity member 4.

$$\lambda 1 = L1/[L/\lambda - L2/\lambda 2] \tag{2}$$

λ: thermal conductivity (W/mK) of honeycomb structure
λ1: corrected thermal conductivity (W/mK) of honeycomb structure
λ2: thermal conductivity (W/mK) of high-thermal-conductivity member
L: total thickness (m) of honeycomb structure and two high-thermal-conductivity members provided at two end of honeycomb structure
L1: thickness (m) of honeycomb structure
L2: thickness (m) of high-thermal-conductivity member The high-thermal-conductivity member 4 may be a film formed by applying, on the contact faces of the ends 11 and 12 of the honeycomb structure, a paste containing a high-thermal-conductivity substance (powder) such as carbon, silver or the like (the paste is obtained, for example, by kneading the powder with an organic solvent represented by acetone). The paste my be applied on the contact face of the end (11, 12) of the honeycomb structure and/or on the contact face (211, 222) of each contact member (21, 22). By applying the paste, the gap formed between the above contact face can be filled as well and good thermal conduction can be obtained.

By setting the contact pressure when the contact member 2 is in contact with the honeycomb structure 1 or with the high-thermal conductivity member 4, at 1 to 10 kg/cm², the gap formed between the contact face can be filled and good thermal conduction can be obtained.

In the present embodiment, measurement of thermal conductivity can be made preferably when the honeycomb structure to be measured is made of a material having a thermal conductivity of 1 (W/mK) or more. Particularly when measurement of thermal conductivity is made using a high-thermal-conductivity member between a honeycomb structure and contact member, thermal conduction is good and the thermal conductivity of a honeycomb structure of high thermal conductivity can be measured at high accuracy. As preferable examples of the material for honeycomb structure, there can be mentioned silicon carbide, a composite material of silicon carbide and metallic silicon, silicon nitride and non-oxides having a relatively high thermal conductivity. The method can preferably applied to oxides when they have a thermal conductivity of 1 W/mK or more.

In measurement of thermal conductivity of a honeycomb structure, it is also preferred that, as shown in FIG. 2, the exposed portion 13 of the side of a honeycomb structure 1 is covered with a heat-insulating material 5. Covering it with the heat-insulating material 5 suppresses heat dissipation from the exposed side portion 13 during measurement of thermal conductivity, whereby measurement of thermal conductivity can be made at high accuracy. As the heat-insulating material, there can be mentioned, for example, a polyurethane mat and a polystyrene foam. The area to be covered with the heat-insulating material may be not only the exposed side portion 13 but also the whole portion including the contact members 2. It is also preferred to surround the honeycomb structure with the honeycomb structures made of the same material in place of using the heat-insulating material, because it is effective for making homogeneous the heat flow in the honeycomb structure.

EXAMPLES

The present invention is described more specifically by way of Examples. However, the present invention is not restricted to these Examples.

Examples 1 to 7

There were produced, by ordinary extrusion molding, two kinds of honeycomb structures made of metallic silicon-bonded silicon carbide (silicon carbide bonded with metallic silicon) and having a rib thickness of 15 mil and a cell density of 200 cpsi (cells per square inch) or 300 cpsi.

A block of 35 mm×35 mm×25 mm was cut out from each of the two kinds of honeycomb structures and measured for thermal conductivity by a steady method, using neither high-thermal-conductivity member nor heat-insulating material, as shown in FIG. 1. Each block was measured for thermal conductivity by the steady method using both or either of high-thermal-conductivity members and a heat-insulating material, as shown in FIG. 2. The results are shown in Table 1.

TABLE 1

|  | Example 1 | Example 2 | Example 3 | Example 4 | Example 5 | Example 6 | Example 7 |
| --- | --- | --- | --- | --- | --- | --- | --- |
| High-thermal-conductivity member | Not used | Carbon sheet | Not used | Aluminum foil | Carbon sheet | Not used | Carbon sheet |
| Heat-insulating material | Not used | Not used | Polystyrene foam | Not used | Polystyrene foam | Not used | Polystyrene foam |
| Cell density (cpsi) | 200 | 200 | 200 | 200 | 200 | 300 | 300 |
| Opening ratio (%) | 62 | 62 | 62 | 62 | 62 | 55 | 55 |
| Effective area ratio (%) | 38 | 38 | 38 | 38 | 38 | 45 | 45 |
| Thermal conductivity, converted value (W/mK) | 11 | 11 | 11 | 11 | 11 | 14 | 14 |
| Thermal conductivity, measured value (W/mK) | 4 | 12 | 8 | 8 | 12 | 6 | 15 |

Here, thermal conductivity, converted value means a value obtained by measuring the thermal conductivity of a honeycomb structure by the laser flash method based on JIS R 1611, using a test specimen of particular shape and then multiplying the measured thermal conductivity by an effective area ratio which indicates an effective end face area obtained by subtracting the total opening area of the end face of the honeycomb structure from the area of the end face, to convert the measured thermal conductivity into the thermal conductivity of the honeycomb structure per se. The thermal conductivity of a honeycomb structure measured by the laser flash method includes an error associated with the porosity, etc. but has certain accuracy; therefore, the measured thermal conductivity in the present Examples was evaluated in comparison with the thermal conductivity measured by the laser flash method.

As shown in Table 1, the thermal conductivity of a honeycomb structure can be measured by a steady temperature method. As indicated in Examples 1 and 6, the measurement of thermal conductivity is possible even when neither high-thermal-conductivity member nor heat-insulating material is used; however, a value nearer to that of the laser flash method is obtainable by using an aluminum foil or a carbon sheet as high-thermal-conductivity members or a polystyrene foam as a heat-insulating material (Examples 2 to 5 and 7).

In the present Examples, preparation of a flat plate of 10 mm×10 mm×1 mm or less is not necessary and measurement of thermal conductivity can be made using a test specimen of block shape; therefore, workability of sample preparation is improved and the time for sample preparation is shortened.

INDUSTRIAL APPLICABILITY

As described above, according to the present method for measurement of thermal conductivity of a honeycomb structure measurement is possible in a shape of a honeycomb structure per se or in a block shape and preparation of, for example, a test specimen of particular shape is not necessary. As a result, the operability of thermal conductivity measurement is improved and the time for sample preparation (processing) is shortened.

The invention claimed is:
1. A method for measurement of thermal conductivity of a honeycomb structure having an axial direction, two ends, and a plurality of through-holes surrounded by partition walls extending in the axial direction, the method comprising the steps of:
contacting the two ends of the honeycomb structure with contact members;
covering exposed sides of the honeycomb structure with heat-insulating material;
keeping the whole honeycomb structure in a steady temperature state with keeping two ends of the honeycomb structure at given different temperatures; and
measuring a thermal conductivity of the honeycomb structure in the steady state,
wherein:
the contact members are kept at given different temperatures and are contacted with the two ends of the honeycomb structure to keep the two ends of the honeycomb structure at given different temperatures;
the two ends of the honeycomb structure and the contact members are contacted with each other via high-thermal-conductivity members; and
each high-thermal-conductivity member is made of a film formed by applying a paste containing a substance of high thermal conductivity, on a contact face of the honeycomb structure and/or the contact member.

2. The method for measurement of thermal conductivity of a honeycomb structure according to claim 1, wherein the thermal conductivity $\lambda$ (W/mK) of the honeycomb structure is calculated from the following expression (1):

$$\lambda = QH \cdot [L/(T1-T2)] \tag{1}$$

where the thermal conductivity $\lambda$(W/mK) of the honeycomb structure is specified in relation to:
an amount of heat flow QH (W/m$^2$)=[(Q1+Q2)/2], each of Q1 (W/m$^2$) and Q2 (W/m$^2$) being obtained by measuring an amount of heat flow at each contact member using a heat flow meter connected with the contact member;
a distance L (m) between the two ends of the honeycomb structure; and
temperatures T1 (K) and T2 (K) of the two ends of the honeycomb structure in the steady temperature state of the whole honeycomb structure.

3. The method for measurement of thermal conductivity of a honeycomb structure according to claim 2, wherein a sheet having flexibility is used as the high-thermal-conductivity member.

4. The method for measurement of thermal conductivity of a honeycomb structure according to claim 1, wherein a sheet having flexibility is used as the high-thermal-conductivity member.

5. The method for measurement of thermal conductivity of a honeycomb structure according to claim 1, wherein a contact pressure between the contact member and the end of the honeycomb structure is set at 1 to 10 kg/cm2.

6. The method for measurement of thermal conductivity of a honeycomb structure according to claim 1, wherein the honeycomb structure is made of a material having a thermal conductivity of 1 (W/mK) or more.

7. The method for measurement of thermal conductivity of a honeycomb structure according to claim 1, wherein the honeycomb structure contains at least one kind selected from the group consisting of silicon carbide, a composite of silicon carbide and metallic silicon, and silicon nitride.

8. The method for measurement of thermal conductivity of a honeycomb structure according to claim 1, wherein at least one of the through-holes is plugged at one of the two ends of the honeycomb structure.

\* \* \* \* \*